(12) United States Patent
Klaveness et al.

(10) Patent No.: US 7,198,776 B2
(45) Date of Patent: Apr. 3, 2007

(54) METAL COMPLEX COMPOUNDS

(75) Inventors: Jo Klaveness, Oslo (NO); Pal Rongved, Nesoddtangen (NO)

(73) Assignee: GE Healthcare AS, Oslo (NO)

( * ) Notice: Subject to any disclaimer, the term of this patent is extended or adjusted under 35 U.S.C. 154(b) by 117 days.

(21) Appl. No.: 10/496,852

(22) PCT Filed: Nov. 28, 2002

(86) PCT No.: PCT/NO02/00453

§ 371 (c)(1),
(2), (4) Date: Dec. 16, 2004

(87) PCT Pub. No.: WO03/045442

PCT Pub. Date: Jun. 5, 2003

(65) Prior Publication Data

US 2005/0090653 A1   Apr. 28, 2005

(30) Foreign Application Priority Data

Nov. 28, 2001   (NO) ................................. 20015814

(51) Int. Cl.
*A61B 5/055* (2006.01)
*C07F 5/00* (2006.01)
(52) U.S. Cl. ................ 424/9.364; 424/9.36; 424/9.363; 534/13; 534/16; 546/2
(58) Field of Classification Search ............... 424/9.36, 424/9.363, 9.364; 534/13, 16; 546/2
See application file for complete search history.

(56) References Cited

U.S. PATENT DOCUMENTS

| 5,536,491 A | 7/1996 | Asai et al. ............... 424/9.363 |
| 5,690,909 A | 11/1997 | Platzek et al. ........... 424/9.363 |
| 5,707,605 A | 1/1998 | Meade et al. ............... 424/9.35 |
| 5,980,862 A | 11/1999 | Meade et al. ............... 424/9.35 |

FOREIGN PATENT DOCUMENTS

| WO | 96/38184 | 12/1996 |
| WO | 97/26017 | 7/1997 |
| WO | 99/25389 | 5/1999 |

OTHER PUBLICATIONS

Moats et al., Angew. Chem. Int. Ed. Engl. 1997, 36, 726-728.
H. J. Freisleben, Clinical Hemorheology and Microcirculation, (2000) 23 (2-4) 219-24.
Watson, A.D., Rocklage, S. M. and Carvlin, M. J.: Contrast agents in Stark, D. D. and Bradley, W. G. (Eds.): *Magnetic resonance imaging*. vol. One. Mosby Year Book. St. Louis (1992) 372-437.
Berger et al. (Eds.), NMR Spectroscopy of the non-metallic elements, John Wiley & Sons, Chichester 1997, Chapter 6, p. 398-699.
International Search Report for PCT/NO02/00453 dated Apr. 7, 2003.

*Primary Examiner*—Porfirio Nazario-Gonzalez
(74) *Attorney, Agent, or Firm*—Li Cai

(57) ABSTRACT

The invention relates to metal complex compounds, contrast agents for MRI and in vivo NMR markers for NMR spectroscopy comprising said metal complex compounds and methods for in vivo determination of physiological parameters, e.g. enzyme activity or pH using said metal complex compounds.

8 Claims, No Drawings

METAL COMPLEX COMPOUNDS

This application is a filing under 35 U.S.C. § 371 and claims priority to international application number PCT/NO02/00453 filed Nov. 28, 2002 which claims priority to Norwegian Application 20015814 filed Nov. 28, 2001, the entire disclosure of which is hereby incorporated by reference.

The invention relates to metal complex compounds, contrast agents for MRI and in vivo NMR markers for NMR spectroscopy comprising said metal complex compounds and methods for in vivo determination of physiological parameters, e.g. enzyme activity or pH using said metal complex compounds.

Several in vivo methods, both imaging techniques and non-imaging techniques, can be used in the diagnosis of disease. MRI (magnetic resonance imaging) is a frequently used in vivo imaging technique for the diagnosis of diseases. It is based on the interaction between radio waves and body tissue water protons in a magnetic field. In order to improve the image contrast in soft tissue examinations, contrast agents are commonly used in MRI.

Beside employing contrast agent aided MRI as a tool for diagnosis based on morphology and/or anatomy, several attempts have been made to use said technique for the measurement and the quantification of physiological parameters in order to detect abnormal changes of said physiological changes and enable diagnosis, especially early-stage diagnosis, based on said changes.

U.S. Pat. Nos. 5,707,605, US 5,980,862, WO-A-96/38184 and WO-A-99/25389 disclose MRI contrast agents comprising a complex consisting of a paramagnetic metal ion and a chelator, the complex comprising a moiety covalently attached to said chelator which occupies a coordination site of the paramagnetic metal ion. Said moiety is removed upon reaction with an enzyme and the change of relaxivity is determined. A drawback of the disclosed contrast agents is that the change in relaxivity caused by the enzymatic transformation is relatively small. Inherent differences in concentration may overrule the effect of relaxation changes caused by enzymatic transformation.

Moats et al., Angew. Chem. Int. Ed. Engl. 1997, 36, 726–728 describe a MRI contrast agent comprising gadolinium and galactopyranose which is a substrate for the enzyme β-galactosidase. The enzyme activated cleavage of the galactopyranose moiety and the change of coordination number of gadolinium results only in a small change in relaxivity. When relaxivity changes are of this magnitude, the local concentration of contrast agent in normal tissue and pathological tissue has to be the same (or has to be quantified) to obtain reliable diagnostic results based on differences in enzyme activity.

As $^{19}F$ is a nucleus that is detectable by magnetic resonance (NMR) spectroscopy, fluorinated compounds can be used as contrast agents in MRI and as in vivo NMR markers in NMR spectroscopy. $^{19}F$ is an NMR-active isotope with spin ½ which provides about 83% of the NMR sensitivity of protons. One of the main differences between protons and fluorine in the human or non-human animal body is that fluorine exists only in very low concentrations, predominantly immobilized in the bone matrix. Therefore, no signal background interferes during in vivo investigation of $^{19}F$-NMR or $^{19}F$-MRI.

In U.S. Pat. No. 5,536,491 $^{19}F$-MRI contrast media are described comprising a metal complex compound in which a macro-cyclic polyamine ligand containing fluorine atoms is coordinate-bonded to a paramagnetic metal ion. Said contrast media can be chemically modified to impart tissue specificity (e.g. by forming composites with a tissue specific substance having a specific affinity for a particular tissue) or to detect changes in tissue environment, such as pH or oxygen concentration by determination of change of fluorine chemical shift of the contrast medium. As a drawback, the fluorine atom(s) and the paramagnetic metal atom in the compounds disclosed in U.S. Pat. No. 5,536,491 are too far away from each other and the change in fluorine chemical shift upon change in pH is not enhanced by the influence of the paramagnetic metal ion. As a consequence, change in fluorine chemical shift is relatively low and minor pH changes can not be monitored.

In U.S. Pat. No. 5,690,909, fluorine containing macrocyclic metal complexes that consist of a complexing agent and a paramagnetic metal ion are described. Said complexes can be used as temperature sensors in NMR diagnosis by determining fluorine chemical shift. As the changes in fluorine chemical shift of these complexes are intramolecular in origin and independent of outside influences such as ionic strength, oxygen pressure or pH, said compounds can not be used to detect changes in ionic strength, oxygen pressure or pH.

However, there is still a need for contrast agents that can enable diagnosis in an early stage with good reliability. Useful markers for early stage diagnosis in vivo are physiological parameters such as enzyme activity, pH or the presence/concentration of free radicals. Abnormal enzyme activity of specific enzymes is often observed in cancer or cancer-related diseases, cardiovascular diseases, diseases of the central nervous system and in inflammations and infections. Enzyme activity is usually increased in the diseased area compared to other areas, but may also be decreased in the diseased area. In tumours increased enzyme activity may usually be assumed to result from overexpression of specific genes. Abnormal pH values are associated to several severe diseases. The pH value is usually reduced during cancer diseases, cardiovascular diseases like for example stroke, osteoporosis, inflammation and certain autoimmune diseases. Free radicals are known to be generated in ischemia upon reperfusion. They propagate complications because of oxidative tissue damage, as described by H. J. Freisleben, Clinical Hemorheology and Microcirculation, (2000) 23 (2–4) 219–24. Determination of abnormal physiological parameters and identification of tissue or cells showing abnormal physiological parameters using non-invasive MRI would therefore be a favorable method in early stage diagnosis.

We have now surprisingly found that certain metal complex compounds comprising a paramagnetic metal ion and a chelate, wherein said chelate comprises at least one fluorine atom, can be used to monitor and determine physiological parameters by determining the change in fluorine chemical shift which occurs upon influence of said physiological parameters on the metal complex compounds. It has been found that when the fluorine atom is within certain proximity of the paramagnetic metal atom, physiologic parameters like pH or enzyme activity effect a change in the chemical shift of said fluorine atom. The metal complex compounds can be used as MRI contrast agents or NMR markers for monitoring or detecting physiological parameters, especially abnormal physiological parameters in vivo.

The present invention provides metal complex compounds comprising a paramagnetic chelate comprising a paramagnetic metal ion M and a chelating agent, said chelating agent comprises at least one fluorine atom and a molecular moiety X, wherein the coordination distance between X and M changes upon influence of a physiological parameter and thereby changing the chemical shift of the at least one fluorine atom.

The term "paramagnetic chelate" as used herein refers to a metal complex containing a paramagnetic metal ion and at least one chelating agent.

The term "chelating agent" as used herein refers to chemical compounds that bind to metal atoms, rendering them less likely to bind to other compounds, particularly biological compounds and/or rendering them less toxic.

The metal complex compounds according to the invention comprise preferably a paramagnetic metal ion M selected from the group consisting of divalent and trivalent ions of an element of atomic number 21 to 29, 42, 44 and 57 to 83. Particularly preferred paramagnetic metal ions are $La^{3+}$, $Pr^{3+}$, $Tm^{3+}$, $Dy^{3+}$ $Eu^{3+}$ and $Mn^{2+}$. Especially particularly preferred paramagnetic metal ions M are $La^{3+}$, $Pr^{3+}$, $Tm^{3+}$, $Dy^{3+}$ $Eu^{3+}$.

The chelating agent present in the metal complex compounds according to the invention can be any chelating agent forming stable and physiologically acceptable chelates with the paramagnetic metal ion. The chelating agent can be an acyclic, cyclic or macrocyclic chelating agent. Compounds which could be used as chelating agents for the present invention are described in Watson, A. D., Rocklage, S. M. and Carvlin, M. J.: Contrast agents in Stark, D. D. and Bradley, W. G. (Eds.): *Magnetic resonance imaging*. Volume One. Mosby Year Book. St. Louis (1992) 372–437.

Preferably, the chelating agent is a chelating agent according to formula (I)

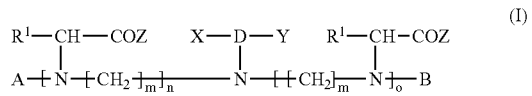

(I)

wherein $R^1$ represents hydrogen or $C_1$–$C_{15}$-alkyl which may optionally be substituted with one or more hydroxy groups, A and B are the same or different and represent $CHR^1R^2$, wherein
  $R^1$ is of the definition as described above and
  $R^2$ represents hydrogen, $C_1$–$C_{20}$-alkyl, $C_6$–$C_{20}$-aryl, $C_6$–$C_{20}$-aralkyl,
    said residues may optionally be substituted with one or more hydroxy groups, or
  A and B form together a bridge $(CH_2)_m$, Z represents $NH_2$, $NHR^2$, OH, $O^-$ or $OR^3$, wherein $R^3$ is a base equivalent or a metal ion equivalent, X represents a molecular moiety whose coordination distance to the paramagnetic metal ion chelated by the chelating agent of formula (1) changes upon influence of a physiological parameter Y represents a fluorine atom or a hydrocarbon group comprising at least one fluorine atom, D represents a saturated or unsaturated straight or branched-chain hydrocarbon group containing 1 to 4 carbon atoms or a phenyl group, m represents an integer from 2 to 3 and n and o are the same or different and represent an integer from 1 to 3.

Preferred chelating agents according to formula (I) are derivatives of polyaminocarboxylates. Particularly preferred chelating agents according to formula (I) are the following compounds, wherein one of the carboxy groups COOH is substituted by the group X-D-Y according to formula (I):

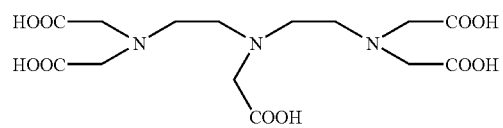

DTPA

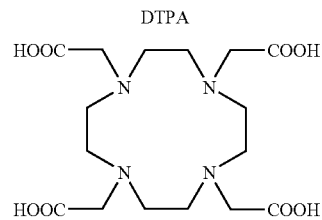

DOTA

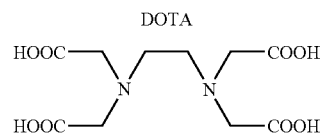

EDTA

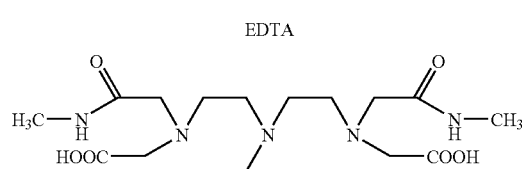

DTPA-BMA

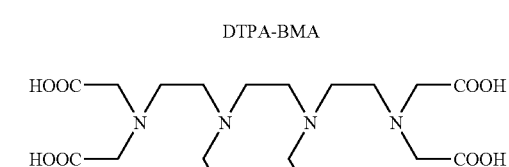

TTHA

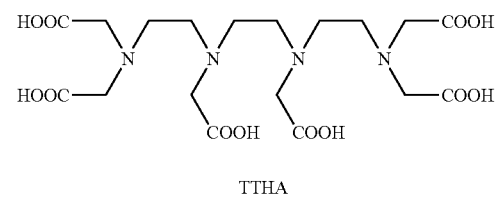

DTPA

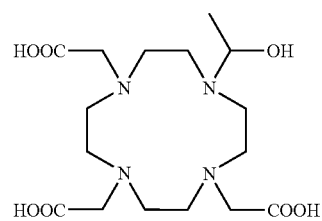

DTPA

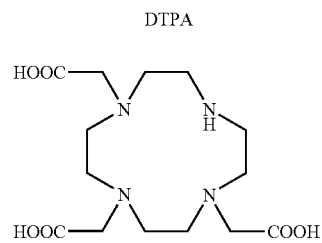

DO3A

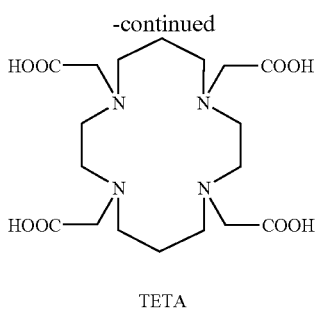

TETA

Especially particularly preferred chelating agents according to formula (I) are DTPA, DOTA and DO3A, wherein one of the carboxy groups COOH is substituted by a group X-D-Y according to formula (I).

Further, the chelating agents comprise at least one fluorine atom and a molecular moiety X, wherein the coordination distance between X and M changes upon influence of a physiological parameter and thereby changing the chemical shift of the at least one fluorine atom. According to NMR theory, the distance d affects the shift according to the following formula:

$$\Delta\delta = K \frac{3\cos\vartheta - 1}{d^3}$$

where Θ is the angle X-M-F where F is the at least one fluorine atom affected by M. The change in shift induced by the paramagnetic metal ion M is dependent on the distance between M and F in the third power.

The metal complex compounds according to the invention comprise preferably a chelating agent that comprises more than one fluorine atom, the fluorine atoms preferably showing fluorine chemical shifts that are essentially the same. Essentially the same means that the chemical shift values of all fluorine atoms are distributed within a sufficiently narrow range, preferably within a range of 50 ppm or less, particularly preferably within the range of 30 ppm or less, so that the signals from all the fluorine atoms are effectively sampled in MRI or NMR measurements.

In a preferred embodiment, the metal complex compounds according to the invention comprise a chelating agent that comprises at least one straight chain or branched chain alkyl group, aryl group or aralkyl group substituted by one or more fluorine atoms, preferably by more than one fluorine atoms. Preferably, the chelating agent comprises at least one fluorine atom or a perfluoroalkyl or perfluoroaryl group in which all hydrogen atoms are substituted by fluorine. The number of carbon atoms in these alkyl, aryl, aralkyl, perfluoroalkyl and perfluoroaryl groups is preferably 1 to 10. The above-mentioned groups may in addition contain one or more functional groups such as hydroxyl groups, amine groups, carbonyl groups or amide groups, or one or more heteroatoms such as N, O or S. Particularly preferably the chelating agent comprises at least one fluorine atom or at least one group selected from the group consisting of trifluoromethyl, perfluoroethyl, 2,2,2-trifluoroethyl, perfluoropropyl, perfluoroisopropyl, bis(trifluoromethyl)methyl, tris(trifluoromethyl)methyl, 2,2,3,3,3-pentafluoropropyl, perfluorobutyl, trifluoromethylphenyl, 1,3-di(trifluoromethyl)phenyl, trifluoromethylbenzyl, 1,3-di(trifluoromethyl)benzyl, tris(trifluoromethyl)methlphenyl, tris(trifluoromethyl)-methylbenzyl, fluorophenyl, difluorophenyl, pentafluorophenyl and pentafluorobenzyl. Especially particularly preferred, the chelating agent comprises at least one fluorine atom or a group selected from the group consisting of trifluoromethyl, tris(trifluoromethyl)methyl and pentafluorophenyl.

In another preferred embodiment, the chelating agent comprises at least one fluorine atom which changes fluorine chemical shift upon influence of a physiological parameter and at least one fluorine atom which does not change fluorine chemical shift upon influence of said physiological parameter. The latter fluorine atom(s) serve(s) as an internal standard.

The metal complex compounds according to the invention further comprise molecular moiety X and the coordination distance between the molecular moiety X and the paramagnetic metal ion M changes upon influence of a physiological parameter.

In a preferred embodiment, the molecular moiety X has a certain affinity to the paramagnetic metal ion M resulting in a certain coordination distance between X and M. The coordination distance is such that the chemical shift of the at least one fluorine atom is influenced. Upon influence of a physiological parameter, the affinity of X to M is reduced, the coordination distance between X and M changes, thus the chemical shift of the at least one fluorine atom changes too. For example, the molecular moiety X having a certain affinity to the paramagnetic metal M might be a negatively charged X group (X⁻). The coordination distance between X⁻ and M is relatively short due to the free electron pair in X which promotes coordination to the positively charged paramagnetic metal ion. Upon influence of a physiological parameter such as pH, X⁻ is protonated at decreasing pH-values resulting in a protonated group XH. XH has a reduced affinity to M which leads to an increased coordination distance between XH and M. The increased coordination distance between XH and M influences the chemical shift of the at least one fluorine atom and the chemical shift of said at least one fluorine atom changes.

Preferred examples of molecular moieties X are electronegative groups comprising at least one free electron pair. Particularly preferably, said molecular moiety X is selected from the group consisting of OH, O⁻, SH, S⁻, COOH, COO⁻, PO(OH)$_2$, PO(OH)O⁻, PO(O)$_2^{2-}$, CONH$_2$, CONH⁻, CONHR$^2$, (CONR$^2$)⁻, NH$_2$, NH⁻, NHR$^2$, (NR$^2$)⁻, NR$^2$R$^4$, NHSO$_2$-Phenyl or (NSO$_2$-Phenyl)⁻, wherein R$^2$ represents hydrogen, C$_1$–C$_{20}$-alkyl, C$_6$–C$_{20}$-aryl, C$_6$–C$_{20}$-aralkyl, said residues may optionally be substituted with one or more hydroxy groups and R$^4$ represents straight or branched chain C$_1$–C$_4$-alkyl, optionally substituted with one or more hydroxy groups or a keto group.

In another preferred embodiment, the molecular moiety X has a low affinity or no affinity to the paramagnetic metal ion M resulting in a relatively large coordination distance between X and M. Upon influence of a physiological parameter, the affinity of X to M is increased, the coordination distance between X and M changes and therefore the chemical shift of the at least one fluorine atom changes. For example, the molecular moiety X having low or no affinity to the paramagnetic metal M might be a methyl group. The coordination distance between methyl and M is relatively large as the methyl group does not coordinate to the positively charged paramagnetic metal ion M. Upon influence of a physiological parameter such as the enzyme cytochrome P 450 (CYP 450), the methyl group is transformed into a carboxy group. Said carboxy group has a higher affinity to M resulting in a decreased coordination distance. Said decrease in coordination distance influences the chemical shift of the at least one fluorine atom and the chemical shift of the said at least one fluorine atom changes. Another example is a molecular moiety X having a certain affinity to M but a relatively large coordination distance due to a shielding group being present in the same molecule providing sterical hinderance. The shielding group can be removed/cleaved off upon influence of a specific enzyme, resulting in a "free" molecular moiety X which then can coordinate to M.

The metal complex compounds according to the invention preferably comprise paramagnetic chelates containing a paramagnetic metal ion selected from the group consisting of $La^{3+}$, $Pr^{3+}$, $Tm^{3+}$, $Dy^{3+}$ $Eu^{3+}$ and $Mn^{2+}$ and a chelating agent selected from the group consisting of DTPA, DOTA, EDTA, DTPA-BMA, TTHA, DTPA, DO3A and TETA, wherein one of the carboxy groups COOH is substituted by a group X-D-Y according to formula (I). Particularly preferred paramagnetic chelates are those containing a paramagnetic metal ions selected from the group consisting of $La^{3+}$, $Pr^{3+}$, $Tm^{3+}$, $Dy^{3+}$ $Eu^{3+}$ and a chelating agent selected from the group consisting of DTPA, DOTA and DO3A, wherein one of the carboxy groups COOH is substituted by a group X-D-Y according to formula (I).

The change in fluorine chemical shift that occurs upon influence of a physiological parameter according to the invention is preferably at least 1 ppm, particularly preferably at least 2 ppm and especially particularly preferably at least 3 ppm. The change in fluorine chemical shift can be upfield or downfield (positive or negative).

Changes in fluorine chemical shift can for example be calculated on shift data according to Berger et al. (Eds.), NMR Spectroscopy of the non-metallic elements, John Wiley & Sons, Chichester 1997, Chapter 6, p. 398–699.

Another aspect of the invention are contrast agents or in vivo NMR markers comprising metal complex compounds according to the invention.

Yet another aspect of the invention is the use of metal complex compounds according to the invention as contrast agents or in vivo NMR markers.

Yet another aspect of the invention is the use of metal complex compounds according to the invention for the manufacture of contrast agents or in vivo NMR markers.

Yet another aspect of the invention is the use of metal complex compounds, contrast agents or in vivo NMR markers according to the invention for the monitoring or detection of physiological parameters, preferably for the monitoring or detection of abnormal physiological parameters.

Yet another aspect of the invention is use of metal complex compounds, contrast agents or in vivo NMR markers according to the invention for the diagnosis of diseases in the human or non-human animal body.

Yet another aspect of the invention is use of metal complex compounds, contrast agents or in vivo NMR markers according to the invention for detection of areas of disease in the human or non-human animal body.

Yet another aspect of the invention is the use of metal complex compounds according to the invention for the manufacture of a contrast agent or in vivo NMR marker for the in vivo detection of abnormal physiological parameters in the human or non-human animal body by determination of change in fluorine chemical shift upon influence of said physiological parameters on said metal complex compounds using $^{19}F$-MRI or $^{19}F$-NMR spectroscopy.

Yet another aspect of the invention is a method of detecting abnormal physiological parameters in vivo said method comprising:
a) administration of a contrast agent or an in vivo NMR marker comprising metal complex compounds according to the invention or a metal complex compound according to the invention to a human or non-human animal body, and
b) determination of abnormal physiological parameters by determining the change in fluorine chemical shift upon influence of said physiological parameter on said metal complex compound, wherein the determination is carried out by means of $^{19}F$-MRI or $^{19}F$-NMR spectroscopy.

Yet another aspect of the invention is a method of detecting abnormal physiological parameters in vivo said method comprising:
a) administration of a contrast agent or an in vivo NMR marker comprising metal complex compounds according to the invention or a metal complex compound according to the invention to a human or non-human animal body, and
b) determination of abnormal physiological parameters by determining the change in fluorine chemical shift upon influence of said physiological parameter on said metal complex compound, wherein the determination is carried out by means of $^{19}F$-MRI or $^{19}F$-NMR spectroscopy, said method being used for the diagnosis of diseases in the human or non-human animal body or for detecting an area of disease in the human or non-human animal body.

According to the invention, the physiological parameters are preferably pH, enzyme activity or free radicals, particularly preferably pH and enzyme activity.

Preferably, the metal complex compounds according to the invention comprise a molecular moiety X that is affected by pH and/or the change of pH, e.g. said molecular moiety X is protonated or deprotonated.

This is illustrated in the following scheme. Here, the paramagnetic metal ion is a preferred trivalent lanthanide ion. The coordination distance d between X and $La^{3+}$ will be dependent on pH. Said distance will determine the influence on the fluorine chemical shift of the at least one fluorine atom in the group Y, as defined in formula (I) above.

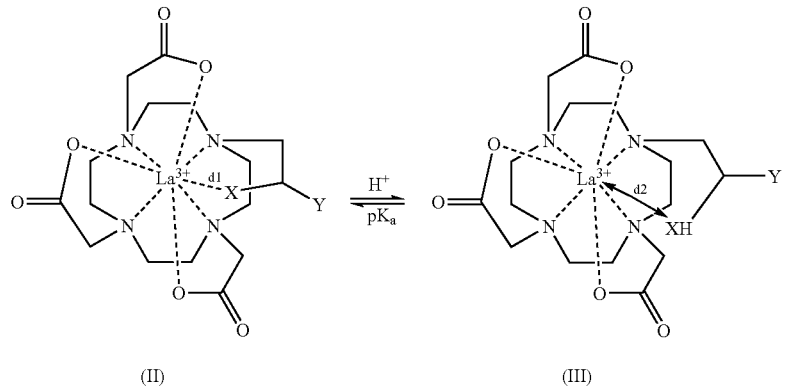

(II)　　　　　　　(III)

-continued

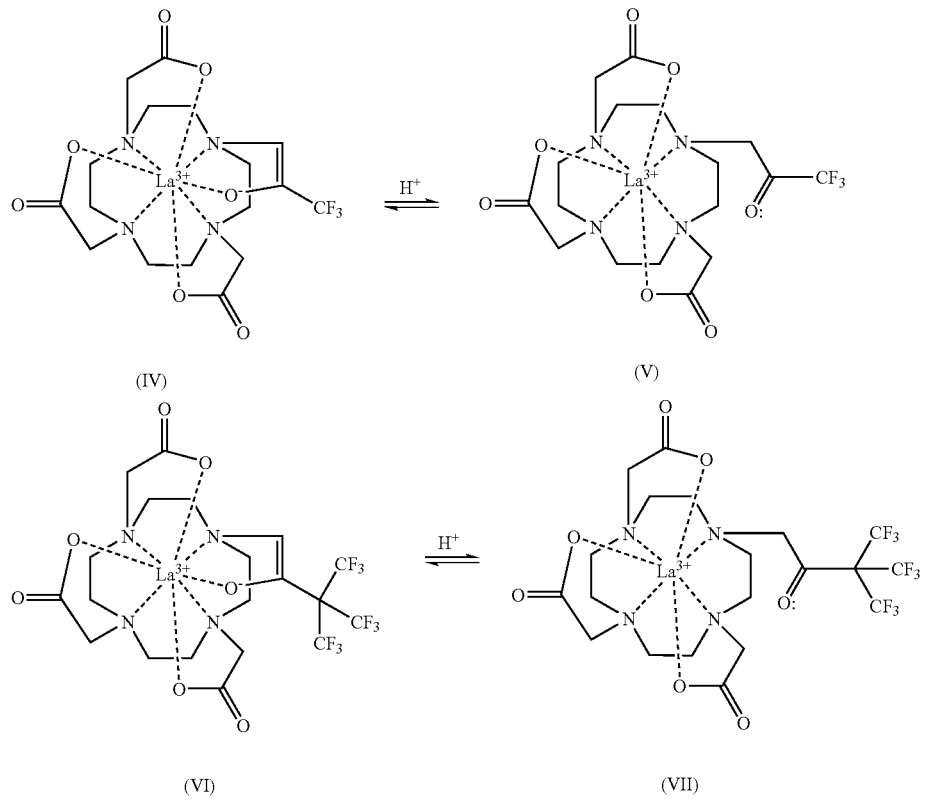

(IV)  (V)

(VI)  (VII)

Formulae (II) to (VII) are preferred examples of metal complex compounds according to the invention where the fluorine chemical shift will be significantly affected by the change in coordination distance between M and X. The protonation of X in formula (II) or the O⁻-group in formulae (IV) and (VI) with decreasing pH is characterized by a $pK_a$ value. This $pK_a$ value is preferably adapted to the physiologically relevant pH range by the incorporation of electron donating or withdrawing groups. Particularly preferred $pK_a$ values are 3–8, especially preferred is 6–7.

Other preferred metal complex compounds according to the invention wherein the coordination distance between X and M will be dependent on pH are the following compounds according to formulae (VIII) and (IX), wherein Y is as defined above:

Metal complex compounds according to the invention wherein the coordination distance between X and M changes upon influence of pH can be used as contrast agents or in vivo NMR markers or can be used for the manufacture of contrast agents or in vivo NMR markers. Such contrast agents/in vivo NMR markers are preferably used for in vivo monitoring of pH, preferably for the detection of abnormal pH, said detection of abnormal pH being preferably used in the diagnosis of diseases in the human or non-human animal body or in the detection of areas of disease in the human or non-human animal body.

Metal complex compounds according to the invention wherein the coordination distance between X and M changes upon influence of enzyme activity comprise a molecular moiety X that is an enzyme substrate which reacts with a

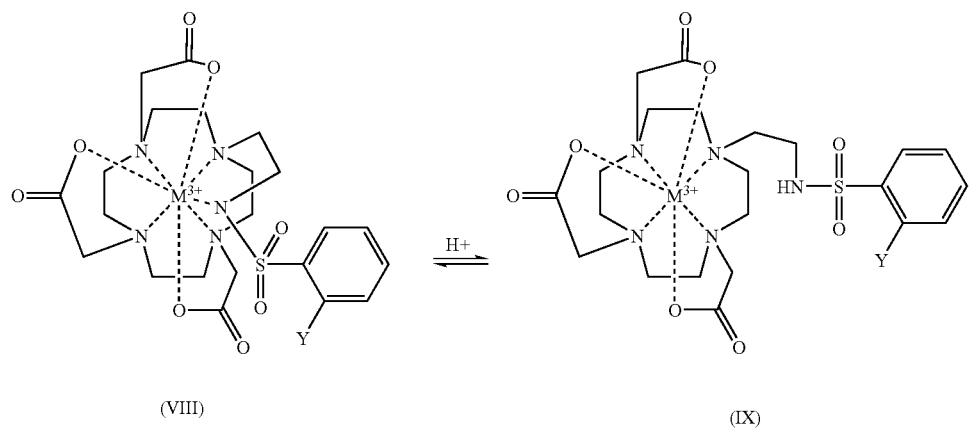

(VIII)  (IX)

specific enzyme and thereby changes the coordination distance between the molecular moiety X and the paramagnetic metal ion M.

The metal complex compound according to the invention comprises preferably an enzyme substrate for the following enzymes or subgroups of the following enzymes: alkaline phosphatase, aromatase, N-acetylglucosaminyltransferase, 17-alpha-hydroxylase/17,20-lysae (CYP17), cathepsin D, cyclooxygenase, cysteine protease, dihydropyrimidine dehydrogenase (DPD), farnesyltransferase, fucosyltransferase, glutamyl hydrolase, glutathione S-transferase, glycogen phosphorylase (GP), lipoxygenase, 12-lipoxygenase, matrix metalloproteinase, nitric oxide synthetase, oestradiol 17β-hydroxy steroid dehydrogenase, proteolytic enzymes in general, phosphatases, phospholipase C, phosphodiesterase (PDE 1), phospholipid phosphatase, protein kinase C, pyruvate kinase, ribonucleases (acid RNases), steroid sulphatase, stearyl-CoA desaturase, testosterone 5-alpha-reductase, thymidyl synthetase, topoisomerase, telomerase and tyrosine kinase. These enzymes are associated with cancer and detection of abnormal activity of said enzymes using metal complex compounds comprising enzyme substrates for said enzymes or contrast agents/in vivo NMR markers comprising said metal complex compounds can be favourable for early non-invasive diagnosis of cancer.

In a particular preferred embodiment the metal complex compound according to the invention comprises an enzyme substrate for the following enzymes: cyclooxygenase, farnesyltransferase, matrix metallo-proteinases, topoisomerase and telomerase. Metal complex compounds comprising an enzyme substrate for said enzymes or contrast agents/in vivo NMR markers comprising said metal complex compounds are particularly preferred for detection of abnormal activity of said enzymes for diagnosis of cancer and cancer related diseases.

In another preferred embodiment, the metal complex compound according to the invention comprises an enzyme substrate for the following enzymes: angiotensin—converting enzyme (ACE), $Ca^{(2+)}$—transporting ATPase, hydroxymethylglutaryl-CoA reductase, cyclic AMP-dependant protein kinase, endopeptidases, endothelial constitutive nitric oxide synthetase, inducible nitric oxide synthetase, nitric oxide synthetase, cyclooxygenase 2, prostaglandin endoperoxide synthetase, aspartic endopeptidase, endothelin converting enzyme, beta-adrenergic receptor kinase, G-protein-coupled receptor kinase-3, G-protein-coupled receptor kinase-5, protein-serine-threonine kinase, peptidyl-dipeptidase A, 3',5'-cyclic-GMP phosphodiesterase, protein kinase C, esterase, aryldialkylphosphatase, creatine kinase, dopamine beta-hydroxylase, fatty acid desaturase, serine endopeptidase, phosphoprotein phosphatase, acetyl-CoA carboxylase, cystathionine beta-synthase, methylenetetrahydrofolate reductase, superoxide dismutase, paraoxonase, thrombin, plasmin, factor VIIa, factor IXa, factor Xa, streptokinase, urokinase and plasminogen activator. These enzymes are associated with cardiovascular diseases and detection of abnormal activity of said enzymes using metal complex compounds comprising enzyme substrates for said enzymes or contrast agents/in vivo NMR markers comprising said metal complex compounds can be favourable for early non-invasive diagnosis of cardiovascular diseases.

In a particular preferred embodiment the metal complex compound according to the invention comprises an enzyme substrate for the following enzymes: angiotensin converting enzyme (ACE), hydroxymethylglutaryl-CoA reductase, endothelial constitutive nitric oxide synthetase, endothelin converting enzyme, protein serine-threonine kinase, phosphoprotein phosphatase, superoxide dismutase, thrombin, plasmin, plasminogen activator and lipoprotein lipase. Metal complex compounds comprising enzyme substrates for said enzymes or contrast agents/in vivo NMR markers comprising said metal complex compounds are particularly preferred for detection of abnormal activity of said enzymes for diagnosis cardiovascular diseases, preferably for diagnosis of cardiac failure, myocardial infarction, atherosclerosis, thrombosis, embolism, aneurysms, stroke and hemorrhage, particularly preferably for diagnosis of atherosclerosis, myocardial infarction and thrombosis.

In another preferred embodiment, the metal complex compound according to the invention comprises an enzyme substrate for the following enzymes: protein kinases, phosphopyruvate hydratase, $Ca^{(2+)}$-transporting ATPase, amonihydrolases, aspartocyclase, nitric oxide synthetase, choline O-acetyltransferase, monoamine oxydase, beta-1,4-galactosyl transferase, myelin basic protein kinase, cyclooxygenase-2, endothelial constitutive nitric oxide synthetase, amino-acid neurotransmitters, phosphoprotein phosphatase, alkaline phosphatase, nucleotidase, catechol O-methyltransferase, glutamyl carboxylase, glutamate translocase, glutamate decarboxylase, acetylcholinesterase, tyrosine 3-monooxygenase, peptide hydrolases, aminopeptidase and hydrolases. These enzymes are associated with diseases of the central nervous system and detection of abnormal activity of said enzymes using metal complex compounds comprising enzyme substrates for said enzymes or contrast agents/in vivo NMR markers comprising said metal complex compounds can be favourable for early non-invasive diagnosis of central nervous system diseases.

In a particularly preferred embodiment the metal complex compound according to the invention comprises an enzyme substrate for the following enzymes: protein kinases, nitric oxide synthase, monoamine oxydase, myelin basic protein kinase, phosphoprotein phosphatase, glutamate translocase, tyrosine 3-monooxygenase and hydrolases. Metal complex compounds comprising an enzyme substrate for said enzymes or contrast agents/in vivo NMR markers comprising said metal complex compounds are particularly preferred for detection of abnormal activity of said enzymes for diagnosis of central nervous system diseases.

In a particular preferred embodiment the metal complex compound according to the invention comprises an enzyme substrate for the following enzymes: matrix metalloproteinase, phosphodiesterase 4, nitric oxide synthetase, gelatinase B. These enzymes are associated with multiple sclerosis and detection of abnormal activity of said enzymes using metal complex compounds comprising an enzyme substrate for said enzymes or contrast agents/in vivo NMR markers comprising said metal complex compounds can be favourable for early non-invasive diagnosis of multiple sclerosis.

In another preferred embodiment, the metal complex compound according to the invention comprises an enzyme substrate for the following enzymes: choline-O-acetyl-transferase, cyclooxygenase-2, matrix metalloproteinase, protease, nitric-oxide synthetase, phospholipase A2, acetylcholinesterase, calpain and endopeptidases. These enzymes are associated with Alzheimer's disease and detection of abnormal activity of said enzymes using metal complex compounds comprising an enzyme substrate for said enzymes or contrast agents/in vivo NMR markers comprising said metal complex compounds can be favourable for early non-invasive diagnosis of Alzheimer's disease.

In a particular preferred embodiment the metal complex compound according to the invention comprises an enzyme substrate for the following enzymes: matrix metalloproteinase, protease and calpain. Metal complex compounds comprising an enzyme substrate for said enzymes or contrast agents/in vivo NMR markers comprising said metal complex compounds are particularly preferred for detection of abnormal activity of said enzymes for diagnosis of Alzheimer's disease.

In another preferred embodiment, the metal complex compound according to the invention comprises an enzyme substrate for the following enzymes: alkaline phosphatase, acid phosphatase, tartrate-resistant acid phosphatase, metalloendopeptidase, collagenases, nitric-oxide synthetase and aromatase. These enzymes are associated with bone diseases and detection of abnormal activity of said enzymes using metal complex compounds comprising an enzyme substrate for said enzymes or contrast agents/in vivo NMR markers comprising said metal complex compounds can be favourable for early non-invasive diagnosis of bone diseases.

In a particular preferred embodiment the metal complex compound according to the invention comprises an enzyme substrate for the following enzymes: alkaline phosphatase, acid phosphatase and collagenases. Metal complex compounds comprising an enzyme substrate for said enzymes or contrast agents/in vivo NMR markers comprising said metal complex compounds are particularly preferred for detection of abnormal activity of said enzymes for diagnosis of bone diseases, preferably for diagnosis of osteolytic diseases, particularly preferably for diagnosis of osteoporosis, osteopetrosis and osteosclerosis.

In another preferred embodiment, the metal complex compound according to the invention comprises an enzyme substrate for the following enzymes: alpha-glucosidase, RNA replicase, andopeptidase, cystein endopeptidase, DNA helicase, herpes simplex thymidine kinase (HSV-TK), serine endopeptidase, influenza A and B viral neuramidase, hepatitis C virus helicase, viral NS3 serine protease, RNA helicase, RNA dependent RNA polymerase, ribonucleotide reductase, viral protease, viral kinase, HIV reverse transcriptase, viral integrase, RNA-directed DNA polymerase and alanine transaminase. These enzymes are associated with viral infections and detection of abnormal activity of said enzymes using metal complex compounds comprising an enzyme substrate for said enzymes or contrast agents/in vivo NMR markers comprising said metal complex compounds can be favourable for early non-invasive diagnosis of viral infections.

In a particular preferred embodiment the metal complex compound according to the invention comprises an enzyme substrate for the following enzymes: RNA replicase, endopeptidase, DNA helicase, viral neuamidase HIV reverse transcriptase, viral integrase and protease. Metal complex compounds comprising an enzyme substrate for said enzymes or contrast agents/in vivo NMR markers comprising said metal complex compounds are particularly preferred for detection of abnormal activity of said enzymes for diagnosis of viral infections.

In another preferred embodiment, the metal complex compound according to the invention comprises preferably an enzyme substrate for the following enzymes: beta-lactamase, carbohydrate dehydrogenase, aryl and alkyl transferase, peptide synthease, serine endopeptidase, topoisomerase, muramidase, acetyltransferase, phosphotransferase, MASP-2 protease, MBP-associated serine protease and amidohydrolase. These enzymes are associated with bacterial infections and detection of abnormal activity of said enzymes using metal complex compounds comprising an enzyme substrate for said enzymes or contrast agents/in vivo NMR markers comprising said metal complex compounds can be favourable for early non-invasive diagnosis of bacterial infections.

In a particular preferred embodiment the metal complex compound according to the invention comprises an enzyme substrate for the following enzymes: beta-lactamase, serine endopeptidase and muramidase. Metal complex compounds comprising an enzyme substrate for said enzymes or contrast agents/in vivo NMR markers comprising said metal complex compounds are particularly preferred for detection of abnormal activity of said enzymes for diagnosis of bacterial infections.

In another preferred embodiment, the metal complex compound according to the invention comprises preferably an enzyme substrate for the following enzymes: TOR kinase, 1,3-beta-glucan synthetase, lysophospholipase, calcineurin, chitin synthetase, phospholipase, beta-N-acetylhexoaminidase, $H^{\oplus}$-ATPase, glycylpeptide-N-myristoyl transferase and methyltransferase. These enzymes are associated with fungal infections and detection of abnormal activity of said enzymes using metal complex compounds comprising an enzyme substrate for said enzymes or contrast agents/in vivo NMR markers comprising said metal complex compounds can be favourable for early non-invasive diagnosis of fungal infections.

In a particular preferred embodiment the metal complex compound according to the invention comprises an enzyme substrate for the following enzymes: 1,3-beta-glucan synthetase, calcineurin, chitin synthetase and glycylpeptide-N-myristoyl transferase. Metal complex compounds comprising an enzyme substrate for said enzymes or contrast agents/in vivo NMR markers comprising said metal complex compounds are particularly preferred for detection of abnormal activity of said enzymes for diagnosis of fungal infections.

In another particularly preferred embodiment the metal complex compound according to the invention comprises an enzyme substrate for transglutaminase (protein-glutamine-γ-glutamyl transferase). This enzyme catalyzes the exchange of the —$NH_2$ group of glutamine with the 6-amino group of lysine, releasing ammonia and forming protein cross-links, ultimate forming a network of densely cross-linked proteins. Transglutaminases comprise a class of enzymes. The most familiar member is Factor XIIIa, which creates cross-links between fibrin molecules in blood clot formation. The other transglutaminases are usually lumped together as "tissue transglutaminases". Transglutaminases are known to act on two substrates, a lysine side chain and a glutamine side chain.

In particularly preferred embodiment the metal complex compound according to the invention comprises an enzyme substrate for transglutaminases which comprises lysine and/or glutamine. In a further particularly preferred embodiment the metal complex compound comprises an enzyme substrate for transglutaminases which comprises a "lysine mimic" preferably a lysine mimic selected from the group consisting of straight chain hydrocarbons containing a primary amino group at the end of the chain, preferably a straight chain hydrocarbon containing four or more, particularly preferably five or more carbon atoms, straight chain hydrocarbons containing more than one amine groups such as putrescine and cadaverine and derivatives thereof such as dansylcadaverine. In a further particularly preferred embodiment the metal complex compound according to the invention comprises an enzyme substrate for transglutaminases which comprises a lysine related amino acid, preferably a lysine related amino acid selected from the group consisting of ornithine, 2,4-diaminobutyric acid, hydroxylysine, N(6)- methyllysine, N(2)-methyllysine and 2,7-diaminoheptanoic acid. Of the above mentioned amino acids, D- as well as L-enantiomers can be used.

In a further particularly preferred embodiment the metal complex compound according to the invention comprises an enzyme substrate for transglutaminase which comprises a glutamine containing peptide. The glutamine-containing peptide will always include the amino acid glutamine and/or homologues of glutamine possessing four or more carbon atoms, for instance asparagine, 2-amino-adipic acid-6-amide, glutamic acid analogues substituted with alkyl (e.g., methyl) on one or more nitrogens, e.g. glutamic acid 5-methylamide. It is generally recognized that the peptide must be at least a dipeptide, for instance Gln-Gly which is blocked at the N-terminus. In a preferred embodiment, the glutamine containing peptide is benzyloxycarbonyl-L-glutamylglycine. In another preferred embodiment the glutamine containing peptide is the decapeptide amide Leu-Gly-Leu-Gly-Gln-Gly-Lys-Val-Leu-Gly-NH$_2$. Said decapeptide amide has been found to be a good substrate for Factor XIIIa as well as for tissue transglutaminase from pig liver.

In another particularly preferred embodiment the metal complex compound according to the invention comprises an enzyme substrate for caspases. Caspases are a family of aspartate-directed proteases. Activation of caspases proceeds by a cascade mechanism, one of the last to be activated is caspase-3. Caspases cleave a number of important intracellular proteins, including several protein kinases, components of the DNA repair machinery, and structural elements of the cytoplasm and nucleus.

In particularly preferred embodiment the metal complex compound according to the invention comprises an enzyme substrate for caspases which comprises a peptide comprising an aspartate residue, particularly preferably an aspartate residue preceded by a sequence of four to five amino acids. Said sequence of four to five amio acids preferably contain another aspartate residue or glutamate residue making it acidic. Said sequence of four to five amino acids further preferably contain valine or other amino acid containing an aliphatic hydrophobic side chain such as leucine or isoleucine.

Metal complex compounds comprising an enzyme substrate for transglutaminases and caspases or contrast agents/in vivo NMR-markers comprising said metal complex compounds are preferably used for the diagnosis of apoptosis and/or necrosis.

Apoptosis is the internal programmed process of cell death inactivating the genetic material and crucial parts of the metabolic machinery. Necrosis is the pathological process of destruction of tissue due to external insults, although there is no dividing line between apoptosis and necrosis. In mature individuals, apoptosis of large numbers of cells within a small volume of tissue will frequently be a sign of disease, while apoptosis of single cells (for instance, senescent granulocytes) occurs continuously. Apoptosis is initiated by signals which may either be external (i.e., tumour necrosis factor-α or Fas ligand) or internal. Internal signals may be generated by failure of repair mechanisms for DNA damage (e.g., p53), loss of adhesion to the substrate, or stress factors such as low pH, low energy supply, or UV light. The process proceeds through several distinctive steps, including loss of mitochondrial membrane potential, release of signal proteins from the mitochondria, activation of a class of specific intracellular proteinases, the caspases, and fragmentation of DNA. A consequence of apoptosis is alterations in the structure of the plasma membrane, including exposure of phosphatidylserine head groups on the outer leaflet of the lipid bilayer and appearance of new antigens. These changes serve as signals for phagocytosis of apoptotic bodies by macrophages or other cells.

Apoptosis is crucial to development of neoplasms. During tumour development cells die as a consequence of a failing energy supply as a result of competition with other mutant cells that are better adapted to the environment of the tumour. Apoptotic cells are also found in cardiac infarctions and are predominant in atherosclerotic lesions. Apoptosis may influence the development of the lesion, in particular its progress towards a stable or unstable condition. Unstable atherosclerotic plaques are associated with an increased risk of fragmentation of the plaque, in turn implying thrombi in other parts of the body.

Apoptosis and/or necrosis are also involved in the damage due to cerebral ischemia and degenerative diseases of the central nervous system, such as Alzheimer's and multiple sclerosis. In addition the processes are important in inflammations.

Hence, metal complex compounds comprising an enzyme substrate for transglutaminases or caspases or contrast agents/in vivo NMR markers comprising said metal complex compounds are particularly preferred for detection of abnormal activity of said enzymes for detection of apoptosis and/or necrosis for the diagnosis of neoplastic diseases including malignant as well as non-malignant tumours, cardiovascular diseases including infarctions and thrombosis and degenerative diseases of the central nervous system such as Alzheimer's disease.

In another particularly preferred embodiment the metal complex compound according to the invention preferably comprises an enzyme substrate for hydrolytic enzymes.

In a particularly preferred embodiment the metal complex compound according to the invention comprises alkyl-O—PO$_3^{2-}$ or aryl-O—PO$_3^{2-}$ which are substrates for phosphatases. The reaction of said substrate with phosphatases results in hydrolytic cleavage to alkyl-OH or aryl-OH and PO$_4^{2-}$. Preferably, the metal complex compound according to the invention comprises the following enzyme substrates for phosphatases:

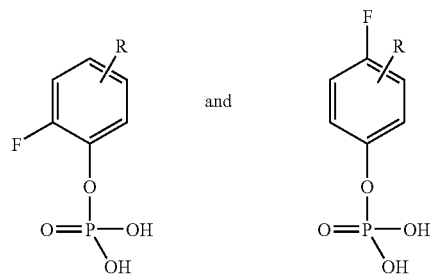

Metal complex compounds comprising alkyl-O—PO$_3^{2-}$ or aryl-O—PO$_3^{2-}$ or contrast agents/in vivo NMR markers comprising said metal complex compounds are particularly preferred for detection of abnormal activity of phosphatases for the diagnosis of cancer or cancer related diseases, preferably for the diagnosis of prostate carcinoma, for the diagnosis of bone diseases, for the diagnosis of some liver diseases and for the diagnosis of thrombocytopenia.

In a further particularly preferred embodiment the metal complex compound according to the invention comprises alkyl-(NH)-(Glu)$_n$ which is a substrate for aminopeptidase A.

The reaction of said substrate with aminopeptidase A results in hydrolytic cleavage to alkyl-$NH_3^+$ and n Glu.

In a further particularly preferred embodiment the metal complex compound according to the invention comprises 4-alkyl-($C^6R^1\ R^2\ R^3\ R^4$)NH-amino acid-$NH_2$, which is a substrate for aminopeptidase, wherein $R^1$–$R^4$ are hydrogen or electronegative groups such as F, Cl, or $NO_2$, said electronegative groups being present in sufficient numbers to ensure that the amino group is minimally protonated at physiological pH. The reaction of said enzyme substrate with aminopeptideas results in hydrolytic cleavage to 4-alkyl-($C^6R^1\ R^2\ R^3\ R^4$)$NH_2$ and amino acid. The change in charge will depend on the charge of the amino acid residue (e.g., Lys or Arg would result in the loss of two positive charges).

Metal complex compounds comprising alkyl-(NH)-(Glu)$_n$ which is a substrate for aminopeptidase A or 4-alkyl-($C_6R^{1}\ R^2\ R^3\ R^4$)NH-amino acid-$NH_2$, which is a substrate for aminopeptidase or contrast agents/in vivo NMR markers comprising said metal complex compounds are particularly preferred for detection of abnormal activity of said enzymes for the diagnosis of central nervous system diseases.

In a further particularly preferred embodiment the metal complex compound according to the invention comprises 4-alkyl-($C_6H_4$)—CO-amino acid-$CO_2H$ which is a substrate for carboxypeptidase. The reaction of said enzyme substrate with carboxypeptidase results in hydrolytic cleavage to 4-alkyl-($C_6H_4$)—$CO_2^-$ and amino acid.

Metal complex compounds comprising 4-alkyl-($C_6H_4$)—CO-amino acid-$CO_2H$ or contrast agents/in vivo NMR markers comprising said metal complex compounds are particularly preferred for detection of abnormal activity of carboxypeptidases for the diagnosis of cardiovascular diseases.

In a further particularly preferred the metal complex compound according to the invention comprises 4-alkyl-$C_6H_4$—$CH_2$—$NH_3^+$ which is a substrate for monoamine oxidase. The reaction of said enzyme substrate with monoamine oxidase requires the presence of water and oxygen and results in hydrolytic cleavage to 4-alkyl-$C_6H_4$—CHO, $H_2O_2$ and $NH_4^+$.

Metal complex compounds comprising 4-alkyl-$C_6H_4$—$CH_2$—$NH_3^+$ or contrast agents/in vivo NMR markers comprising said metal complex compounds are particularly preferred for detection of abnormal activity of monoamine oxidase for the diagnosis of central nervous system diseases.

In a further particularly preferred embodiment the metal complex compound according to the invention comprises 1-alkyl-β-O-glucuronic acid which is a substrate for β-glucuronidase. The reaction of said enzyme substrate with β-glucuronidase results in hydrolytic cleavage to alkyl-OH and glucuronic acid. Analogous reactions may be devised for other enzymes such as e.g. galacturonidase or iduronidase.

Metal complex compounds comprising 1-alkyl-β-O-glucuronic acid or contrast agents/in vivo NMR markers comprising said metal complex compounds are particularly preferred for detection of abnormal activity of β-glucuronidase for the diagnosis of diabetes mellitus, renal diseases, pancreatic cancer and liver diseases.

Besides hydrolytic cleavage there are many chemical modifications that may occur upon reaction of the metal complex compound according to the invention comprising an enzyme substrate with a specific enzyme. The following chemical modifications are included:

Hydrolytic Cleavage
  Proteolysis
    Extracellular: metalloproteinases, prostate-specific antigen, collagenases
    Intracellular: lysosomal enzymes, proteasomes, calpain, caspases
  Peptidases (carboxypeptidases, aminopeptidases)
  Hydrolysis of phosphate esters (phospholipases C and D, phosphatases)
  Hydrolysis of esters (lipases, esterases, phospholipases A and B, cholinesterases)
  Amylases: Hydrolysis of glycogen
  Glycosidases: glucuronidases, glucosidases, galactosidases, galacturonidases, mannosidases, sialidases, lactase
  Hydrolysis of sulfate esters: arylsulfatase
  Hydrolysis of nucleic acids: RNAses, DNAses Chemical Reactions of Intermediate Metabolism
  Reactions catalyzed by lactate dehydrogenase, glycogen phosphorylase, methylmalonyl-CoA mutase, lecithin:cholesterol acyltransferase or porphobilinogen deaminase Biosynthetic
  Formation of prostaglandins and thromboxanes from arachinonic acid
  Synthesis of telomers (chromosome ends)
  Farnesylation, geranylgeranylation, myristoylation, palmitoylation, GPI-anchoring and other hydrophobic modifications of proteins
  DNA repair enzymes
  Ubiquitination
  Glycosylation of proteins, usually at asparagine or serine/threonine
  Transfer of sugar moieties, usually from phosphate ester derivatives: glucosyltransferases, fucosyltransferases, galactosyltransferases
  Formation of thioether bonds: gluthathione S-transferases
  Formation of sulfate esters and sulfonamides: sulfo-transferases Reactions Involved in Signalling Pathways:
  Nitric oxide synthetase
  Formation of phosphate esters at serine, threonine or tyrosine in proteins: protein kinases
  Hydrolysis of phosphate esters in protein: protein phosphatases
  Angiotensin converting enzyme
  Endothelin converting enzyme
  Deamination of neurotransmitters: monoamine oxidase
  Cyclization of ATP: adenylate cyclase Miscellaneous
  Topoisomerases (DNA unwinding enzymes)
  Hydroxylations of steroids and aromatic compounds, including detoxification reactions: CYP 17, cytochrome P-450

In another particularly preferred embodiment the metal complex compound according to the invention comprises an enzyme substrate for COX (cyclooxygenase). COX is the key enzyme in the metabolism of arachidonic acid and formation of prostaglandins. There are at least two distinct isoforms of COX, COX 1 and COX 2. Particularly preferred, the metal complex compound according to the invention comprises arachidonic acid as an enzyme substrate for COX Metal complex compounds comprising an enzyme substrate for COX or contrast agents/in vivo NMR markers comprising said metal complex compounds are preferably used for the diagnosis of inflammation, cancer and central nervous diseases such as Alzheimer's disease.

In another particularly preferred embodiment the metal complex compound according to the invention comprises an enzyme substrate for telomerase. Telomerase is a ribonucleoprotein which catalyzes the formation of telo-repeats represented by the nucleic acid sequence TAGGG at the end of chromosomes in vertebrates. The activity of telomerase is increased in a large number of neoplastic diseases. Based on this elevated activity of telomerase in tumours this enzyme has gained interest as a potential cancer marker and as target for future anticancer therapy. Metal complex compounds for diagnosis of cancer based on telomerase activity or contrast agents/in vivo NMR markers comprising said metal complex compounds comprise preferably nucleic acids.

In another particularly preferred embodiment the metal complex compound according to the invention comprises an enzyme substrate for farnesyltransferase or geranylgeranyltransferase. Farnesyltransferase catalyzes the modification of Ras-proteins, enabeling them to attach to the inner surface of plasma membranes. Ras-proteins are guanine nucleotide-binding proteins that play an important role in the control of cell growth. An activation of Ras proteins might result in uncontrolled cell growth and cancer. It is known that Ras proteins play an important role in development of approximately 30% of human cancers including cancers in pancreas and colon. An activation of Ras proteins starts with attachment of the proteins to the inner surface of the plasma membrane. The protein attaches in a modified form, the modification being catalyzed by farnesyltransferase, as mentioned above. Metal complex compounds according to the invention comprising an enzyme substrate for farnesyltransferase or contrast agents/in vivo NMR marker comprising said metal complex compounds can be used for the detection of farnesyltransferase activity and therefore for the identification/diagnosis of cancer at a very early stage. The metal complex compounds according to the invention or the contrast agents/in vivo NMR markers comprising said metal complex compounds preferably comprise isoprene derivatives, preferably farnesyl diphosphate analogues for the detection of farnesyltransferase activity.

Beside farnesyltransferase, several other enzymes mediate transfer of hydrophobic residues to proteins, or removal of such residues as myristic or palmitic acids. Examples are palmitoyl-protein transferase, myristoyl-protein transferase, glycosyl-phosophatidylinositol transferase, and palmitoyl-protein thioesterase. Their activities are known to be modified in specific diseases. Myristoyl-protein transferase activity is increased in colon cancer, glycosyl-phosophatidylinositol transferase is increased in certain protozoic infections and may be involved in prion diseases of the central nervous system. Table 1 lists enzymes that mediate hydrophobic modifications of proteins, the related diseases/conditions and processes involved.

TABLE 1

Diseases or conditions related to hydrophobic modifications of proteins

| Process | Enzyme/pathway | Disease/condition |
| --- | --- | --- |
| Palmiltoylation | Palmitoyl-protein thioesterase | Infantile neuronal ceroid lipofuscinosis |
| Proteolysis | Ubiquitin-proteasome | Metabolic acidosis |
| Proteolysis | Ubiquitin-proteasome | Neurodegerative |
| Proteolysis | Ubiquitin-proteasome | Cancer |
| Farnesylation | Farnesyl protein transferase | Medullablastoma |

TABLE 1-continued

Diseases or conditions related to hydrophobic modifications of proteins

| Process | Enzyme/pathway | Disease/condition |
| --- | --- | --- |
| Farnesylation | Farnesyl protein transferase | Hepatic carcinogenesis |
| Farnesylation | Farnesyl protein transferase | Ceroid lipofuscinosis (Batten's disease) |
| Geranylgeranylation | Geranylgeranol transferase | Prostatic hyperplasia |
| Myristoylation | Myristoyl protein transferase | HIV infection |
| Myristoylation | N-myristoyl transferase | Colon cancer |
| GPI-anchoring | GPI transferase | Paroxysmal nocturnal hemoglobinuria |
| GPI-anchoring | GPI transferase | Carbonic anhydrase deficiencies (osteopetrosis) |
| GPI-anchoring | GPI transferase | Prion diseases of the CNS |
| GPI-anchoring | GPI transferase | Protozoiasis |

Note:
GPI, glycosyl-phosphatidylinositol

In another particularly preferred embodiment the metal complex compound according to the invention comprises an enzyme substrate for phospholipases, preferably an enzyme substrate for phospholipase $A_2$, lipoprotein-associated phospholipase $A_2$ and phospholipase $C_\beta$.

Metal complex compounds according to the invention comprising an enzyme substrate for phospholipase $A_2$ or contrast agents/in vivo NMR markers comprising said metal complex compounds can be used for the diagnosis of inflammation.

Metal complex compounds according to the invention comprising an enzyme substrate for lipoprotein-associated phospholipase $A_2$ or contrast agents/in vivo NMR markers comprising said metal complex compounds can be used for the detection of platelet activating factor, an enzyme which is increasingly expressed in atherosclerosis lesions.

In another particularly preferred embodiment the metal complex compound according to the invention comprises an enzyme substrate for DNA repair enzymes. The genome cannot remain functional without a full complement of DNA repair enzymes (e.g., about ten thousand N-glycosidic bonds between base and deoxyribose are broken each day, either spontaneously or through damage). These are enzymes that comprise a heterogeneous assortment of activities: removal of altered bases, excision of damaged nucleotides, filling in of gaps in the nucleotide sequence and nucleotide mismatch repair. Detection of alterations in the activity of DNA repair enzymes will be valuable in the diagnosis of cancer.

In another particularly preferred embodiment the metal complex compound according to the invention comprises an enzyme substrate for topoisomerases, preferably an enzyme substrate for topoisomerase which comprises one or more nucleic acids, nucleic acids fragments or analogues thereof. Topoisomerases are nuclear enzymes which catalyze breaking of transient DNA strands allowing the cell to manipulate the topology of DNA. Topoisomerase enzymes are essential for DNA replication, transcription and other critical nuclear process in cells. There are two forms of the enzyme, topoisomerase I and topoisomerase II. These enzymes are present in all cells. Metal complex compounds comprising an enzyme substrate for topoisomerases or contrast agents/in vivo NMR markers comprising said metal complex compounds can be used for the diagnosis of cancer.

In another particularly preferred embodiment the metal complex compound according to the invention comprises an enzyme substrate for lysosomal enzymes such as cathepsins, lipases or glycosidases. Turnover of intracellular proteins occurs mainly in two distinct classes of organelles, lysosomes and proteasomes. Entire sections of cytoplasm enter in lysosomes by the process of autophagy, and the components are broken down by the action of lysosomal enzymes such as the cathepsins; lipids and oligosaccharides are degraded by lipases and glycosidases, respectively. For many of these enzymes, synthetic substrates are well known The activity of the autophagic-lysosomal pathway is increased in neoplastic cells, including many tumors, therefore, metal complex compounds comprising enzyme substrates for said enzymes or contrast agents/in vivo NMR markers comprising said metal complex compounds can be used for diagnosis of cancer.

In another particularly preferred embodiment the metal complex compound according to the invention comprises an enzyme substrate for matrix metalloproteinases (MMPs), preferably collagenes, proteoglycans, laminin, fibronectin, gelatins, elastin, perlacan, entactin, vitronectin, tenascin, nidogen, dermatan sulphate, pro-TNF-α, aggrecan, transin, decorin, glycoproteins or molecular moieties or analogues of said compounds which could be used as an enzyme substrate for matrix metalloproteinases. MMPs are a family of 17 zinc-dependent endopeptidases and these endopeptidases degrade essentially all extracellular matrix components. Tumor invasion including metastasis are often associated with increased expression of MMPs. Further on, increased expression of MMPs is often found in multiple sclerosis.

In another particularly preferred embodiment the metal complex compound according to the invention comprises an enzyme substrate for lipase, preferably a triglyceride. Increased levels of lipase are associated with acute pancreatitis and some other diseases located in the abdomen.

In another particularly preferred embodiment the metal complex compound according to the invention comprises an enzyme substrate for 17-a-hydroxylase/17,20-lyase (CYP), preferably a pregnane precursor.

Inherited defects in enzyme molecules are by far the largest category of heritable diseases. As expected, the kind and severity of disease varies greatly. In some populations, one individual in a hundred may be affected by a specific heritable enzyme deficiency. In the diagnosis of defects in enzyme molecules it is often important to localize the areas a specific enzyme is not expressed. This could be done by the methods according to the invention. A patient may for example show neurological symptoms, but the primary affected organ could be the liver. Many of the enzymes given in the following list have been studied in detail, see Scriver et al in "The metabolic basis of inherited disease", $6^{th}$ Edn., McGraw-Hill, New York 1989. Artificial substrates for these enzymes are available and metal complex compounds comprising said artificial substrates or contrast agents/in vivo NMR markers comprising said metal complex compounds can be used to detect said enzymes for the diagnosis of inherited defects.

Enzymes that are Known to be Defective in Various Inherited Diseases:

Enzymes Causing Pharmacogenic Disorders
    Isoniazid acetylase
    Pseudocholinesterase
    Glucose 6-phosphate dehydrogenase Disorders of Carbohydrate Metabolism
    Fructokinase
    Fructose 1,6-diphosphate aldolase B
    Fructose 1,6-diphosphatase
    Glucose 6-phosphatase
    Glucose 6-phosphate translocase
    α-Glucosidase (lysosomal)
    Amylo-1,6-glucosidase
    Amylo-1,4:1,6-glucantransferase
    Gycogen phosphorylase
    Phosphorylase b-kinase
    Phosphofructokinase
    Glycogen synthase
    Phosphoglycerate kinase
    Phosphoglycerate mutase
    Lactate dehydrogenase
    Glucose phosphate isomerase
    Galactose-1-phosphate uridyltransferase
    Galactokinase
    Uridine diphosphate galactose 4-epimerase
    L-xylulose reductase Disorders of Amino Acid Metabolism
    Phenylalanine hydroxylase
    Dihydropteridine reduktase
    Guanosine triphosphate cyclohydrolase
    6-Pyruvoyl tetrahydropterin synthetase
    Fumarylacetoacetate hydrolyase
    Maleylacetoacetate isomerase
    Tyrosine aminotransferase
    Urocanase
    Histidase
    Proline oxidase
    Δ-Pyrrolidine-5-carboxylate dehydrogenase
    4-Hydroxy-L-proline-oxidase
    Peptidase D
    Ornithine-δ-aminotransferase
    Carbamyl phosphate synthase
    Ornithine transcarbamylase
    Argininosuccinic acid synthase
    Argininosuccinic acid synthase
    Arginase
    α-Aminoadipic semialdehyde synthase
    Cysthathionine β-synthase
    α-Cystathionase
    Methionine adenosyltransferase
    Sarcosine dehydrogenase
    Dihydropyrimidine dehydrogenase
    β-Alanine-pyruvate transaminase
    R-β-Aminoisobutyrate-pyruvate transaminase
    Glutamic acid decarboxylase
    GABA-α-Ketoglutarate transaminase
    Succinic semialdehyde dehydrogenase
    Carnosinase Disorders of Metabolism of Organic Acids
    Homogentisic acid oxidase
    Isovaleryl-CoA dehydrogenase
    3-Methylcrotononyl-CoA carboxylase
    3-Methylglutaconyl-CoA hydratase
    Mevalonate kinase
    2-Methylacetoacetyl-CoA thiolase
    3-Hydroxyisobutyryl-CoA deacylase
    Propionyl-CoA carboxylase
    Methylmalonyl-CoA mutase
    ATP:Cobalamin adenosyltransferase
    Glutaryl-CoA dehydrogenase
    2-Ketoadipic acid dehydrogenase Glutathione synthetase
5-Xoprolinase
γ-Glutamylcysteine synthetase
δ-Glutamyl transpeptidase
Cytochrome oxidase
Fumarase
Pyruvate carboxylase
Long-chain acyl-CoA dehydrogenase
Medium-chain acyl-CoA dehydrogenase
Short-chain acyl-CoA dehydrogenase
Electron transfer flavoprotein:ubiquinone oxidoreductase
Alanine:glyoxylate aminotransferase
D-Glycerate dehydrogenase
Glycerol kinase Disorders of Metabolism of Purines and Pyrimidines
PP-Ribose-P synthetase
Hypoxanthine-guanine phosphoribosyltransferase
Adenine phosphoribosyltransferase
Adenosine deaminase
Purine nucleoside phosphorylase
Myoadenylate deaminase
Xanthine dehydrogenase
UMP synthetase
Pyrimidine 5'nucleotidase
Dihydropyrimidine dehydrogenase Disorders of Lipid Metabolism
Lipoprotein lipase
Lecithin:cholesterol acyltransferase
26-hydroxylase (cholesterol)

Disorders of Metabolism of Porphyrins and Heme
δ-Aminolevulinic acid dehydratase
Porphobilinogen deaminase
Uroporphyrinogen cosynthase
Uroporphyrinogen decarboxylase
Coproporphyrinogen oxidase
Protoporphyrinogen oxidase
Ferrochelatase
Bilirubin UDPglucuronyl transferase
Phytanic acid α-hydroxylase
Catalase Disorders of Lysosomal Enzymes
α-L-iduronidase
Iduronate sulfatase
Heparan-N-sulfatase
α-N-acetylglucosaminidase
Acetyl-CoA-α-glucosaminide acetyltransferase
Acetylglucosamine 6-sulfatase
Ggalactose 6-sulfatase
β-Galactosidase
N-Acetylgalactosamine 4-sulfatase
β-Glucuronidase
UDP:N-Acetylglucosamine:lysosomal enzyme N-acetyl-glucosaminyl-1-phospho-transferase
α-Mannosidase
α-Neuraminidase
Aspartylglucosaminidase
α-L-Fucosidase
Acid lipase
Acid ceramidase
Sphingomyelinase
Glucocerebrosidase
Galactosylceramidase
Steroid sulfatase
Arylsulfatase
α-Galactosidase
α-N-Acetylgalactosaminidase
Acid β-galactosidase
β-Hexosaminidase Disorders of Metabolism of Hormones
Steroid 21-hydroxylase
Steroid 5α-reductase
3-β-Hydroxysteroid sulfatase
25(OH)D$_3$-1-α-hydroxylase Disorders of Metabolism of Vitamins
Methylene tetrahydrofolate reductase
Glutamate formiminotransferase
Holocarboxylase synthetase
Biotinidase Disorders of Blood
Cytochrome b$_5$ reductase
Pyruvate kinase
Hexokinase
Glucosephosphate isomerase
Aldolase
Triosephosphate isomerase
Phosphoglycerate kinase
2,3-Diphosphoglyceromutase
6-Phosphogluconate dehydrogenase
Gluthathione peroxidase
Gluthathione reductase
Gluthathione synthetase
γ-Glutamylcysteine synthetase Disorders of the Immune System
Adenosine deaminase
Pyrimidine nucelotidase
Myeloperoxidase
NADPH oxidase Disorders of Connective Tissues
Lysyl hydroxylase
Collagenase
Alkaline phosphatase
Carbonic anhydrase Disorders of Skin
Tyrosinase Disorders of Digestion
Lactase
Trehalase In another particularly preferred embodiment the metal complex compound according to the invention comprises an enzyme substrate for glucose 6-phosphate dehydrogenase, lactate dehydrogenase, L-xylulose reductase, phenylalanine hydroxylase, fumarylacetoacetate hydrolyase, histidase, peptidase D (prolidase), carbamyl phosphate synthase, ornithine transcarbamylase, argininosuccinic acid synthase, argininosuccinase, arginase, carbamyl phosphate synthase, ornithine transcarbamylase, argininosuccinic acid synthase, arginase, methylmalonyl-CoA mutase, ATP:cobalamin adenosyltransferase, 2-ketoadipic acid dehydrogenase, medium-chain acyl-CoA dehydrogenase, hypoxanthine-guanine phosphoribosyltransferase, myoadenylate deaminase, xanthine dehydrogenase, porphobilinogen deaminase, catalase, α-L-iduronidase, iduronate sulfatase, heparan-N-sulfatase, α-N-acetylglucosaminidase, acetyl-CoA-α-glucosaminide acetyltransferase, acetylglucosamine 6-sulfatase, glucocerebrosidase, arylsulfatase, α-galactosidase, acid β-galactosidase, β-hexosaminidase, steroid 21-hydroxylase, 3-β-hydroxysteroid sulfatase, biotinidase, pyruvate kinase, and myeloperoxidase. Most preferred are glucose 6-phosphate dehydrogenase, phenylalanine hydroxylase, argininosuccinase, medium-chain acyl-CoA dehydrogenase, hypoxanthine-guanine phosphoribosyltransferase, lipoprotein lipase, steroid 21-hydroxylase or myeloperoxidase. Metal complex compounds comprising an enzyme substrate for the above-mentioned enzymes or contrast agents/in vivo NMR markers comprising said metal complex compounds can be used for the diagnosis of enzyme defections in various inherited diseases.

The following chelating agents E-Q are particularly preferred chelating agents, wherein the coordination distance between X and M changes upon enzymatic activity:

E is

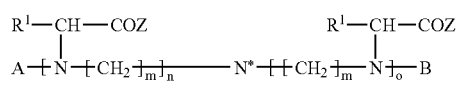

and Q is one of the following residues with Q being bound to E via the nitrogen-atom N*:

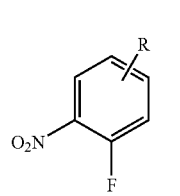

(A)

(B1)

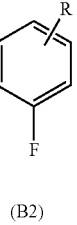

(B2)

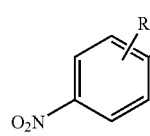

(C)

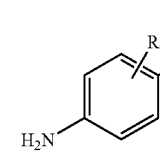

(D1)

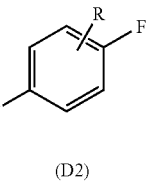

(D2)

-continued

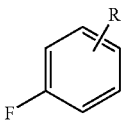 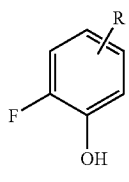

(E)　　　　　　　　(F)

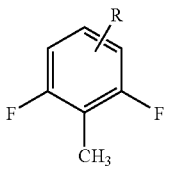 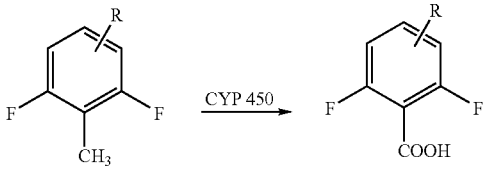

(G)　　　　　　　　(H)

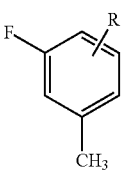 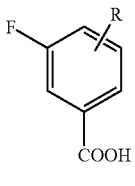

(I)　　　　　　　　(J)

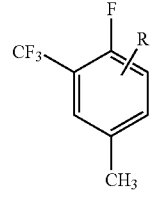 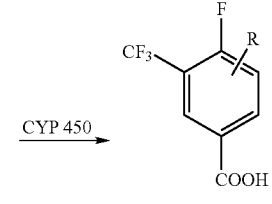

(K)　　　　　　　　(L)

The CF$_3$-group does not change fluorine chemical shift upon influence of CPY 450 and serves as an internal standard.

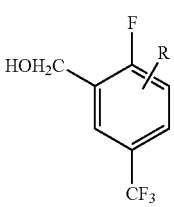 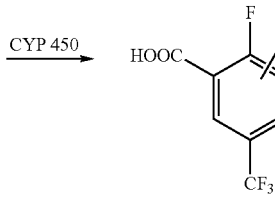

(M)　　　　　　　　(N)

The CF$_3$-group does not change fluorine chemical shift upon influence of CPY 450 and serves as an internal standard.

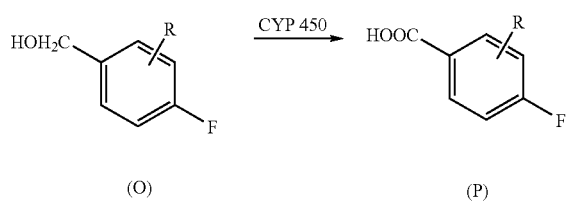

R is one functional group or more functional groups that the same or different, for example hydrophilic or lipophilic groups, pharmacophores, receptor binding moieties or other biologically acceptable groups.

Particularly preferred chelating agents E-Q are those with Q selected from the group consisting of (A) to (O) and E selected from the group consisting of DTPA, DOTA or DO3A, wherein one carboxy group COOH is substituted by one of the compounds (A) to (O). Preferably, said chelating agents form paramagentic chelates with a paramagnetic metal ion selected from the group consisting of $La^{3+}$, $Pr^{3+}$, $Tm^{3+}$, $Dy^{3+}$ and $Eu^{3+}$.

An especially particularly preferred paramagnetic chelate according to the invention is the following compound that is preferably used to detect cytochrome P 450 (CYP 450) activity:

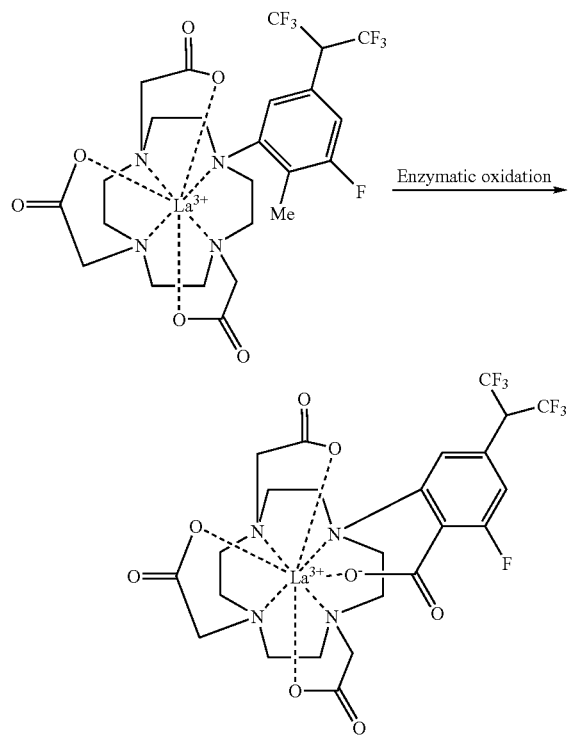

Upon the enzymatic oxidation of the methyl group and coordination of the carboxy group to the paramagnetic metal ion, the influence on the shift of the fluorine atom is large and in the order >10 ppm. The shifts of the fluorine atoms in the perfluoroisopropyl group will be negligible because of the long distance from the shift probe. Hence, the perfluoroisopropyl group serves as an internal standard.

Further preferred chelating agents according to formula (I), wherein the coordination distance between X and M changes upon influence of enzyme activity contain the following groups X-D-Y, wherein E, D and Y are defined as above:

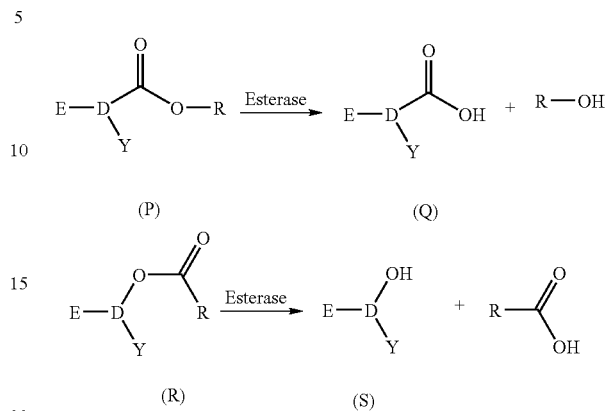

Particularly preferably, compounds (P) to (S) are bound to E, wherein E is DTPA, DOTA or DO3A, wherein one carboxy group COOH is substituted by one of the compounds (P) to (S). Said chelating agents form particularly preferably paramagentic chelates with a paramagnetic metal ion selected from the group consisting of $La^{3+}$, $Pr^{3+}$, $Tm^{3+}$, $Dy^{3+}$ and $Eu^{3+}$.

The metal complex compound or the contrast agent/in vivo NMR marker comprising said metal complex compound according to the invention comprising an enzyme substrate can comprise as an enzyme substrate synthetic organic compounds, naturally occurring compounds or semi-synthetic compounds. The metal complex compound or the contrast agent/in vivo NMR marker comprising said metal complex compound comprise for instance peptides, peptido-mimetics, fatty acids, proteins, carbohydrates or biological precursors thereof, which may contain one or more of the following functional groups: alcohols, phenols, esters including esters with other acids than carboxylic acids, amides, amines, mercapto-groups, aromatic rings and heterocyclic ring systems. The overall structure of the enzyme substrate can be cyclic or linear.

Metal complex compounds according to the invention wherein the coordination distance between X and M changes upon influence of enzyme activity can be used as contrast agents or in vivo NMR markers or can be used for the manufacture of contrast agents or in vivo NMR markers. Such contrast agents/in vivo NMR markers can preferably be used for in vivo detection of enzyme activity, preferably for the detection of abnormal enzyme activity, said detection of abnormal enzyme activity being preferably used for the diagnosis of diseases in the human or non-human animal body or for detecting areas of disease in the human or non-human animal body.

In a further preferred embodiment the metal complex compounds according to the invention further comprise a targeting vector.

A targeting vector according to the present invention is a molecular moiety that enables targeting of the metal complex compounds to a specific site in the human or non-human animal body, preferably located in the area of disease. Said specific sites are, for example, receptors, cells and cell compartments. Preferably, the targeting vector enables targeting of the metal complex compounds according to the invention to a specific receptor, preferably to a tumour specific receptor. In a particularly preferred embodiment, the targeting vector is a molecular moiety showing affinity for a tumour specific receptor.

A metal complex compound according to the invention further comprising a targeting vector or a contrast agent/in vivo NMR marker comprising said metal complex compound should show enhanced residence time at the area of disease.

The metal complex compound according to the invention or the contrast agent/in vivo NMR marker comprising said metal complex compound can be a water-soluble or water-insoluble molecule, e.g. a compound with limited solubility in water so that the compound has to be administered as a powder or a suspension in the methods according to the invention. The molecular weight of the metal complex compound or the contrast agent/in vivo NMR marker comprising said metal complex compound varies and can be low (50–2000) or high (above 2000).

When the metal complex compound according to the invention carries an overall charge, it may be used in the form of a salt with a physiologically acceptable counterion, for example an ammonium, substituted ammonium, alkali metal or alkaline earth metal cation or an anion deriving from an inorganic or organic acid.

The metal complex compound according to the invention or the contrast agent/in vivo NMR marker comprising said metal complex compound used for diagnosis is preferably formulated in conventional pharmaceutical or veterinary parenteral administration form, e.g. suspensions, dispersions, etc., for example in an aqueous vehicle such as water for injections.

The metal complex compound or the contrast agent/in vivo NMR marker comprising said metal complex compound according to the invention may further contain pharmaceutically acceptable diluents and excipients and formulation aids, for example stabilizers, antioxidants, osmolality adjusting agents, buffers or pH-adjusting agents.

The most preferred formulation for the metal complex compounds or the contrast agents/in vivo NMR markers comprising said metal complex compounds used for diagnosis of diseases in the human or non-human animal body is a sterile solution of suspension for intravascular administration or for direct injection into area of interest. Where said metal complex compounds or contrast agents/in vivo NMR markers comprising said metal complex compounds are formulated in a ready-to-use form for parenteral administration, the carrier medium is preferably isotonic or somewhat hypertonic.

The dosage of the metal complex compounds or contrast agents comprising said metal complex compounds used in the diagnosis of diseases in the human or non-human animal body will depend upon the clinical indication, the contrast generating species and the means by which contrast enhancement occurs.

While the metal complex compounds according to the invention or contrast agents/in vivo NMR markers comprising said metal complex compounds according to the invention are particularly suitable for the diagnosis of diseases in the human or non-human animal body involving parenteral administration, e.g. into the vasculature or directly into an organ or muscle tissue, intravenous administration being especially preferred, administration via a non-parenteral route is also applicable, e.g. transdermal, nasal, sub-lingual administration or administration into an external body cavity, e.g. the gastro-intestine tract, the bladder, the uterus or the vagina. The present invention is deemed to extend to cover such administration.

In another aspect the methods according to the invention can be used for follow up therapy. If therapeutic treatment of a disease results in change of a physiological parameter e.g. in an increase/a decrease of one or more specific enzymes, the success of said therapeutic treatment can easily be followed up by the methods according to the invention.

In yet another aspect the methods according to the invention can be used for the selection of drug therapy. If it was for example stated that an increased/decreased enzyme activity is responsible for a certain disease said abnormal enzyme activity could be selected as a target for drug therapy. Preferably, the methods according to the invention are first used for the selection of drug therapy and subsequently for follow up therapy with the selected drug.

In yet another aspect the methods according to the invention can be used for the dosing of drugs in drug therapy. If therapeutic treatment of a disease targets for example one or more specific enzymes, the activity of said enzyme(s) should be increased/decreased by said drug therapy the methods according to the invention can be used to determine if the drug therapy is carried out using a proper dose of said drug.

In a preferred embodiment, the methods of the invention are in a first step used for the diagnosis of disease and the selection of drug therapy and in a second step for the dosing of drugs in drug therapy as well as for follow up said drug therapy.

EXAMPLES

Example 1 a) Synthesis of 1,4,7-tri-(carboxymethyl)-10-(3-fluoro-2-hydroxypropanoyl)-1, 4,7,10-tetraazacyclododecan 0.5 g (0.84 mmol) of 1,4,7-tri(carboxymethyl-tert-butylester)-1,4,7,10-tetra-azacyclododecan (DO3A-TBE) was added to a jacketed vessel containing 7 ml of THF (tetrahydrofurane). The THF was preheated using a circulating bath to 40° C. 0.162 ml (2.52 mmol) of epifluorohydrin was added followed by the slow addition of 0.129 ml (0.093 mmol) of triethylamine over a five minute period. The reaction mixture was closed and stirred using a magnetic stirrer overnight at 40° C. A further 0.047 ml (0.34 mmol) of triethylamine was added after approximately 17 hours. The reaction was then left to stir for 3 days at 40° C.

2 ml of the reaction mixture (0.24 mmol of material) was concentrated in vacuum (20 mmHg/30° C.) to remove solvent and excess triethylamine. Removal of the protecting groups was done by addition of 5 ml of TFA (trifluoroacetic acid) to the concentrated raw product, this was followed by stirring overnight. The mixture was again concentrated under vacuum (20 mm Hg/30° C.). The raw product was dissolved in 2 ml $H_2O$, the pH adjusted to about 10 using 25% $NH_3$(aq). The mixture was then loaded onto a negative ion exchanger (Biorad AG 1-X8, 200-400 mesh, acetate form). After washing with 500 ml $H_2O$, the product was eluted using 150 ml 3M formic acid. Sequential washing and concentrating with 5 ml $H_2O$ (7×) yielded 0.2 g of a clear oil. MS (ES+): 423.2 (100, [M+H]$^+$ MS data showed the expected molecular ion for this compound. NMR data also supported the given structure.

b) NMR Experiments

All spectra were acquired in 5 mm tubes using a Varian Unity Inova 500 spectrometer (11 Tesla) with a 1H{broad-band} indirect detection, pulsed field gradient probe. Preliminary experiments were done in both D₂O and CD₃OD solvents at various temperatures to establish an optimum time-scale window with respect to the molecule's dynamics but the results on which the structure determination was made and the derived NMR data were all obtained in CD₃OD at 50° C. TMS was used as internal reference for the $^1$H and $^{13}$C spectra and $C_6F_6$ as internal reference for the $^{19}$F spectra. Apart from $^1$H and $^{19}$F directly detected spectra, $^1$H—$^1$H-GCOSY and $^1$H{$^{13}$C}-GHSQC and GHMBC 2D spectra were acquired.

NMR Data $^1$H-NMR: (500 MHz);δ (CD3OD,50IC) 4.46 (d of <u>ABX</u> systems), 4.35 (d of multiplets), 4.13 (AB quartet, J ca.17 Hz), 3.66 (AB quartet, J 18.5 Hz), 3.46–3.57 (broad multiplet), 3.39 (AB quartet, J ca.20 Hz), 3.04–3.28 (broad multiplet). $^{19}$F-NMR: (470 MHz);δ (CD3OD, 50° C.) −231.2 ppm (t J 47.7 Hz of d J 19.6 Hz).

Example 2

Synthesis of the Europium Complex of (1,4,7-tri(carboxymethyl)-10-(3-fluoro-2-hydroxypropanoyl)-1,4,7,10-tetraazacyclododecan)

The europium complex of this ligand was made by dissolving 75 mg ligand (1,4,7-tri(carboxymethyl)-10-(3-fluoro-2-hydroxypropanoyl)-1,4,7,10-tetraazacyclo-dodecan) in 1 ml H₂O, followed by adding 36 mg of EuCl₃ and heating at 50° C. for 5 minutes. MS (ES+): 573,1 (34, [M]). MS data of the mixture showed the characteristic isotopic pattern for the europium complex.

Example 3 a) Synthesis of 1,4,7-tri(carboxymethyl-tert-butyl ester)-10-(3-trifluoro-2-hydroxy-propanoyl)-1,4,7,10-tetraazacyclododecan 2.0 g (3,358 mmol) of 1,4,7-tri(carboxymethyl-tert-butylester)-1,4,7,10-tetraaza-cyclododecan (DO3A-TBE) was added to a jacketed vessel containing 28 ml of THF (tetrahydrofurane). The THF was preheated using a circulating bath at 30° C. 1.23 g (10.07 mmol) of epifluorohydrin was added followed by the slow addition of 0.702 ml (5.04 mmol) of triethylamine over a ten minute period. The reaction mixture was closed tightly and stirred at 30° C., using a magnetic stirrer. The temperature was increased after about 14 hours to 40° C. where it stayed for 9 hours before it was lowered to 20° C. The reaction mixture was then stirred for an additional 24 hours at 20° C. The reaction mixture was concentrated in vacuum (20 mmHg/30° C.) to remove solvent and excess of triethylamine. 2 g of a clear oil were obtained. MS (ES+): 627,3 ([M+H]⁺). MS and NMR both indicated formation of the expected product.

b) NMR Experiments

All spectra were acquired in 5 mm tubes using a Varian Unity Inova 500 spectrometer (11 Tesla) with a 1H{broad-band} indirect detection, pulsed field gradient probe and— for directly detected $^{13}$C—a broad-band{$^1$H} probe. Preliminary experiments were done in both CDCl₃ and DMSO-d6 solvents at various temperatures to establish an optimum time-scale window with respect to the molecule's dynamics but the results on which the structure determination was made and the derived NMR data were all obtained in CDCl₃ at 45° C. TMS was used as internal reference for the $^1$H and $^{13}$C spectra and $C_6F_6$ as internal reference for the $^{19}$F spectrum. Apart from $^1$H, $^{19}$F and $^{13}$C directly detected spectra, $^1$H—$^1$H GCOSY, $^1$H{$^{13}$C} GHSQC 2D spectra and $^{13}$C{$^1$H} DEPT were acquired.

NMR Data $^1$H-NMR: (500 MHz);δ (CDCl₃,45° C.) 4.48–4.78 (broad), 3.43 (AB quartet 17.6 Hz), 3.36–3.53 (broad), 3.33 (s), 3.07–3.26 (broad), 2.80–3.06 (broad multiplets) $^{19}$F-NMR: (470 MHz);δ (CDCl₃,45° C.) −79.4 (d J 7 Hz).

The invention claimed is:

1. A metal complex compound comprising a paramagnetic chelate comprising a paramagnetic metal ion M and a chelating agent, said chelating agent is a chelating agent according to formula (I)

$$A \!-\!\!\left[\!N\!-\!\!\left[\!CH_2\!\right]_{\!m}\!\right]_{\!n}\!\!\!\overset{\overset{\displaystyle R^1-CH-COZ}{|}}{\underset{}{}}\!N\!-\!\!\left[\!\!\left[\!CH_2\!\right]_{\!m}\!\!\right.\!\overset{\overset{\displaystyle X-D-Y}{|}}{\underset{}{}}\!N\!\!\left.\!\right]_{\!o}\!\!\!\overset{\overset{\displaystyle R^1-CH-COZ}{|}}{\underset{}{}}\!\!-\!B \quad (I)$$

wherein
  $R^1$ represents hydrogen or $C_1$–$C_{15}$-alkyl which may optionally be substituted with one or more hydroxy groups,
  A and B are the same or different and represent $CHR^1R^2$, wherein
    $R^1$ is of the definition as described above and
    $R^2$ represents hydrogen, $C_1$–$C_{20}$-alkyl, $C_6$–$C_{20}$-aryl, $C_6$–$C_{20}$-aralkyl, said residues may optionally be substituted with one or more hydroxy groups, or
  A and B form together a bridge $(CH_2)_m$,
  Z represents $NH_2$, $NHR^2$, OH, O⁻ or $OR^3$, wherein $R^3$ is a base equivalent or a metal ion equivalent,
  X represents a molecular moiety whose coordination distance to the paramagnetic metal ion chelated by the chelating agent of formula (I) changes upon influence of enzyme activity, being selected from the group of;
    alkyl-O—$PO_3^{2-}$ or aryl-O—$PO_3^{2-}$ which are substrates for phosphatates,
    alkyl-(NH)-(Glu)n which is a substrate for aminopeptidase A,
    4-alkyl-($C_6R^1R^2R^3R^4$)NH-aminoacid-$NH_2$ wherein $R^1$–$R^4$ are hydrogen or F, Cl or $NO_2$, which is a substrate for aminopeptidase,
    4-alkyl -($C_6H_4$)—CO-aminoacid-$CO_2$H which is a substrate for carboxypeptidase,
    4-alkyl-($C_6H_4$)—$CH_2$-$NH_3^-$ which is a substrate for monoamine oxidase, and
    1-alkyl-β-O-glucoronic acid which is a substrate for β-glucoronidase,
  Y represents a fluorine atom or a hydrocarbon group comprising at least one fluorine atom,
  D represents a saturated or unsaturated straight or branched-chain hydrocarbon group containing 1 to 4 carbon atoms or a phenyl group,
  m represents an integer from 2 to 3 and
  n and o are the same or different and represent an integer from 1 to 3, wherein the coordination distance between X and M changes upon influence of enzymatic activity and thereby changing the chemical shift of the at least one fluorine atom.

2. A metal complex compound according to claim 1 wherein the paramagentic metal ion M is selected from the group consisting of divalent and trivalent ions of an element of atomic number 21 to 29, 42, 44 and 57 to 83.

3. A metal complex compound according to claim 1, wherein said chelating agent comprises at least one straight chain or branched chain alkyl group, aryl group or aralkyl group substituted by one or more fluorine atoms.

4. A metal complex compound according to claim 1, said metal complex compound further comprises a targeting vector.

5. Contrast agents or in vivo NMR markers comprising a metal complex compound according to claim 1.

6. Method of detecting abnormal physiological parameters in vivo comprising:
   a) administration of a contrast agent or an in vivo NMR marker comprising a metal complex compound according to claim 1 or a metal complex compound according claim 1 to a human or non-human animal body, and
   b) determination of abnormal physiological parameters by determining the change in fluorine chemical shift upon influence of said physiological parameters on said metal complex compound, wherein the determination is carried out by means of using $^{19}$F-magnetic resonance imaging (MRI) or $^{19}$F-magnetic resonance (NMR) spectroscopy.

7. Method according to claim 6, said method being used for the diagnosis of diseases in the human or non-human animal body.

8. Method according to claim 6, said method being used for detecting an area of disease in the human or non-human animal body.

* * * * *